US011559641B2

(12) United States Patent
Graboi et al.

(10) Patent No.: US 11,559,641 B2
(45) Date of Patent: *Jan. 24, 2023

(54) METHODS AND SYSTEMS FOR MANAGING A PATIENT MOVE

(71) Applicant: Covidien LP, Mansfield, MA (US)

(72) Inventors: Dan Graboi, Encinitas, CA (US); Peter Doyle, Vista, CA (US)

(73) Assignee: Covidien LP, Mansfield, MA (US)

( * ) Notice: Subject to any disclaimer, the term of this patent is extended or adjusted under 35 U.S.C. 154(b) by 378 days.

This patent is subject to a terminal disclaimer.

(21) Appl. No.: 16/831,265

(22) Filed: Mar. 26, 2020

(65) Prior Publication Data

US 2020/0222645 A1 Jul. 16, 2020

Related U.S. Application Data

(60) Continuation of application No. 15/155,595, filed on May 16, 2016, now Pat. No. 10,639,441, which is a
(Continued)

(51) Int. Cl.
*A61M 16/00* (2006.01)
*A61M 16/08* (2006.01)
(Continued)

(52) U.S. Cl.
CPC .... *A61M 16/0051* (2013.01); *A61M 16/0003* (2014.02); *A61M 16/0057* (2013.01);
(Continued)

(58) Field of Classification Search
CPC .......... A61M 16/0875; A61M 16/0051; A61M 16/0021; A61M 16/0022; A61M 16/0024; A61M 2205/14; A61M 2205/3561
See application file for complete search history.

(56) References Cited

U.S. PATENT DOCUMENTS 4,127,123 A 11/1978 Bird
4,448,192 A 5/1984 Stawitcke et al.
(Continued)

FOREIGN PATENT DOCUMENTS

EP 982043 3/2000
EP 1491227 12/2004
(Continued)

OTHER PUBLICATIONS

7200 Series Ventilator, Options, and Accessories: Operator's Manual. Nellcor Puritan Bennett, Part No. 22300 A, Sep. 1990, pp. 1-196.
(Continued)

*Primary Examiner* — Margaret M Luarca

(57) ABSTRACT

This disclosure describes systems and methods for managing a move of a patient being monitored or treated by a medical system, such as a medical ventilator. The disclosure describes a novel approach for preventing a patient from being moved from a first location to second different location that is connected to a monitoring and/or treatment system, before all of the necessary hoses have been disconnected from the patient. Further, the disclosure describes a novel approach of ensuring that all of the necessary hoses are reconnected to a patient being monitored or treated by a monitoring and/or treatment system after being moved from the first location to the second different location.

20 Claims, 7 Drawing Sheets

Related U.S. Application Data division of application No. 13/793,981, filed on Mar. 11, 2013, now Pat. No. 9,358,355.

(51) Int. Cl.
*A61M 16/04* (2006.01)
*G16H 40/63* (2018.01)
*G16H 40/20* (2018.01)
*A61M 16/06* (2006.01)

(52) U.S. Cl.
CPC .......... *A61M 16/024* (2017.08); *A61M 16/04* (2013.01); *A61M 16/06* (2013.01); *A61M 16/0875* (2013.01); *G16H 40/20* (2018.01); *G16H 40/63* (2018.01); *A61M 16/0063* (2014.02); *A61M 2016/0027* (2013.01); *A61M 2016/0033* (2013.01); *A61M 2205/14* (2013.01); *A61M 2205/332* (2013.01); *A61M 2205/3561* (2013.01); *A61M 2205/3569* (2013.01); *A61M 2205/3592* (2013.01); *A61M 2205/505* (2013.01); *A61M 2205/581* (2013.01); *A61M 2205/582* (2013.01); *A61M 2205/583* (2013.01); *A61M 2205/60* (2013.01); *A61M 2205/6054* (2013.01); *A61M 2230/04* (2013.01); *A61M 2230/202* (2013.01); *A61M 2230/205* (2013.01); *A61M 2230/63* (2013.01)

(56) References Cited

U.S. PATENT DOCUMENTS

| | | |
|---|---|---|
| 4,527,557 A | 7/1985 | DeVries et al. |
| 4,637,385 A | 1/1987 | Rusz |
| 4,655,213 A | 4/1987 | Rapoport et al. |
| 4,752,089 A | 6/1988 | Carter |
| 4,773,411 A | 9/1988 | Downs |
| 4,805,612 A | 2/1989 | Jensen |
| 4,805,613 A | 2/1989 | Bird |
| 4,821,709 A | 4/1989 | Jensen |
| 4,921,642 A | 5/1990 | LaTorraca |
| 4,954,799 A | 9/1990 | Kumar |
| 4,986,268 A | 1/1991 | Tehrani |
| 5,044,362 A | 9/1991 | Younes |
| 5,057,822 A | 10/1991 | Hoffman |
| 5,072,737 A | 12/1991 | Goulding |
| 5,107,830 A | 4/1992 | Younes |
| 5,148,802 A | 9/1992 | Sanders et al. |
| 5,150,291 A | 9/1992 | Cummings et al. |
| 5,161,525 A | 11/1992 | Kimm et al. |
| 5,165,398 A | 11/1992 | Bird |
| 5,237,987 A | 8/1993 | Anderson et al. |
| 5,239,995 A | 8/1993 | Estes et al. |
| 5,271,389 A | 12/1993 | Isaza et al. |
| 5,279,549 A | 1/1994 | Ranford |
| 5,299,568 A | 4/1994 | Forare et al. |
| 5,301,921 A | 4/1994 | Kumar |
| 5,307,795 A | 5/1994 | Whitwam et al. |
| 5,313,937 A | 5/1994 | Zdrojkowski |
| 5,319,540 A | 6/1994 | Isaza et al. |
| 5,325,861 A | 7/1994 | Goulding |
| 5,333,606 A | 8/1994 | Schneider et al. |
| 5,339,807 A | 8/1994 | Carter |
| 5,343,857 A | 9/1994 | Schneider et al. |
| 5,351,522 A | 10/1994 | Lura |
| 5,353,788 A | 10/1994 | Miles |
| 5,357,946 A | 10/1994 | Kee et al. |
| 5,368,019 A | 11/1994 | LaTorraca |
| 5,383,449 A | 1/1995 | Forare et al. |
| 5,385,142 A | 1/1995 | Brady et al. |
| 5,390,666 A | 2/1995 | Kimm et al. |
| 5,398,676 A | 3/1995 | Press et al. |
| 5,401,135 A | 3/1995 | Stoen et al. |
| 5,402,796 A | 4/1995 | Packer et al. |
| 5,407,174 A | 4/1995 | Kumar |
| 5,413,110 A | 5/1995 | Cummings et al. |
| 5,433,193 A | 7/1995 | Sanders et al. |
| 5,438,980 A | 8/1995 | Phillips |
| 5,443,075 A | 8/1995 | Holscher |
| 5,452,714 A | 9/1995 | Anderson et al. |
| 5,492,113 A | 2/1996 | Estes et al. |
| 5,507,282 A | 4/1996 | Younes |
| 5,513,631 A | 5/1996 | McWilliams |
| 5,517,983 A | 5/1996 | Deighan et al. |
| 5,520,071 A | 5/1996 | Jones |
| 5,524,615 A | 6/1996 | Power |
| 5,531,221 A | 7/1996 | Power |
| 5,535,738 A | 7/1996 | Estes et al. |
| 5,540,222 A | 7/1996 | Younes |
| 5,542,415 A | 8/1996 | Brady |
| 5,544,674 A | 8/1996 | Kelly |
| 5,549,106 A | 8/1996 | Gruenke et al. |
| 5,551,418 A | 9/1996 | Estes et al. |
| 5,572,993 A | 11/1996 | Kurome et al. |
| 5,582,163 A | 12/1996 | Bonassa |
| 5,596,984 A | 1/1997 | O'Mahoney et al. |
| 5,598,838 A | 2/1997 | Servidio et al. |
| 5,630,411 A | 5/1997 | Holscher |
| 5,632,269 A | 5/1997 | Zdrojkowski |
| 5,632,270 A | 5/1997 | O'Mahoney et al. |
| 5,645,048 A | 7/1997 | Brodsky et al. |
| 5,660,171 A | 8/1997 | Kimm et al. |
| 5,664,560 A | 9/1997 | Merrick et al. |
| 5,664,562 A | 9/1997 | Bourdon |
| 5,671,767 A | 9/1997 | Kelly |
| 5,672,041 A | 9/1997 | Ringdahl et al. |
| 5,673,689 A | 10/1997 | Power |
| 5,692,497 A | 12/1997 | Schnitzer et al. |
| 5,694,923 A | 12/1997 | Hete et al. |
| 5,704,345 A | 1/1998 | Berthon-Jones |
| 5,715,812 A | 2/1998 | Deighan et al. |
| 5,720,278 A | 2/1998 | Lachmann et al. |
| 5,735,267 A | 4/1998 | Tobia |
| 5,743,253 A | 4/1998 | Castor et al. |
| 5,752,506 A | 5/1998 | Richardson |
| 5,762,480 A | 6/1998 | Adahan |
| 5,765,558 A | 6/1998 | Psaros et al. |
| 5,771,884 A | 6/1998 | Yarnall et al. |
| 5,782,233 A | 7/1998 | Niemi et al. |
| 5,791,339 A | 8/1998 | Winter |
| 5,794,615 A | 8/1998 | Estes |
| 5,794,986 A | 8/1998 | Gansel et al. |
| 5,803,065 A | 9/1998 | Zdrojkowski et al. |
| 5,813,399 A | 9/1998 | Isaza et al. |
| 5,823,187 A | 10/1998 | Estes et al. |
| 5,826,575 A | 10/1998 | Lail |
| 5,829,441 A | 11/1998 | Kidd et al. |
| 5,864,938 A | 2/1999 | Gansel et al. |
| 5,865,168 A | 2/1999 | Isaza |
| 5,868,133 A | 2/1999 | DeVries et al. |
| 5,878,744 A | 3/1999 | Pfeiffer |
| 5,881,717 A | 3/1999 | Isaza |
| 5,881,723 A | 3/1999 | Wallace et al. |
| 5,884,622 A | 3/1999 | Younes |
| 5,884,623 A | 3/1999 | Winter |
| 5,901,704 A | 5/1999 | Estes et al. |
| 5,904,141 A | 5/1999 | Estes et al. |
| 5,909,731 A | 6/1999 | O'Mahony et al. |
| 5,915,379 A | 6/1999 | Wallace et al. |
| 5,915,380 A | 6/1999 | Wallace et al. |
| 5,915,382 A | 6/1999 | Power |
| 5,918,597 A | 7/1999 | Jones et al. |
| 5,921,238 A | 7/1999 | Bourdon |
| 5,927,274 A | 7/1999 | Servidio et al. |
| 5,934,274 A | 8/1999 | Merrick et al. |
| 5,957,130 A | 9/1999 | Krahbichler et al. |
| 5,970,975 A | 10/1999 | Estes et al. |
| 5,975,081 A | 11/1999 | Hood et al. |
| 6,024,089 A | 2/2000 | Wallace et al. |
| 6,029,664 A | 2/2000 | Zdrojkowski et al. |
| 6,029,665 A | 2/2000 | Berthon-Jones |
| 6,041,777 A | 3/2000 | Faithfull et al. |
| 6,041,780 A | 3/2000 | Richard et al. |
| 6,047,860 A | 4/2000 | Sanders |

(56) References Cited

U.S. PATENT DOCUMENTS

| | | |
|---|---|---|
| 6,076,523 A | 6/2000 | Jones et al. |
| 6,105,575 A | 8/2000 | Estes et al. |
| 6,116,240 A | 9/2000 | Merrick et al. |
| 6,116,464 A | 9/2000 | Sanders |
| 6,123,073 A | 9/2000 | Schlawin et al. |
| 6,135,105 A | 10/2000 | Lampotang et al. |
| 6,135,106 A | 10/2000 | Dirks et al. |
| 6,142,150 A | 11/2000 | O'Mahony et al. |
| 6,161,539 A | 12/2000 | Winter |
| 6,196,222 B1 | 3/2001 | Heinonen et al. |
| 6,209,540 B1 | 4/2001 | Sugiura et al. |
| 6,213,119 B1 | 4/2001 | Brydon et al. |
| 6,220,245 B1 | 4/2001 | Takabayashi et al. |
| 6,240,919 B1 | 6/2001 | MacDonald et al. |
| 6,253,765 B1 | 7/2001 | Hognelid et al. |
| 6,257,234 B1 | 7/2001 | Sun |
| 6,269,812 B1 | 8/2001 | Wallace et al. |
| 6,273,444 B1 | 8/2001 | Power |
| 6,283,119 B1 | 9/2001 | Bourdon |
| 6,302,105 B1 | 10/2001 | Wickham et al. |
| 6,302,851 B1 | 10/2001 | Gedeon |
| 6,305,372 B1 | 10/2001 | Servidio |
| 6,305,373 B1 | 10/2001 | Wallace et al. |
| 6,305,374 B1 | 10/2001 | Zdrojkowski et al. |
| 6,321,748 B1 | 11/2001 | O'Mahoney |
| 6,325,785 B1 | 12/2001 | Babkes et al. |
| 6,345,619 B1 | 2/2002 | Finn |
| 6,357,438 B1 | 3/2002 | Hansen |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,412,483 B1 | 7/2002 | Jones et al. |
| 6,427,689 B1 | 8/2002 | Estes et al. |
| 6,431,169 B1 | 8/2002 | do Val et al. |
| 6,439,229 B1 | 8/2002 | Du et al. |
| 6,467,477 B1 | 10/2002 | Frank et al. |
| 6,467,478 B1 | 10/2002 | Merrick et al. |
| 6,484,719 B1 | 11/2002 | Berthon-Jones |
| 6,526,970 B2 | 3/2003 | DeVries et al. |
| 6,532,956 B2 | 3/2003 | Hill |
| 6,532,957 B2 | 3/2003 | Berthon-Jones |
| 6,539,940 B2 | 4/2003 | Zdrojkowski et al. |
| 6,546,930 B1 | 4/2003 | Emerson et al. |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,571,795 B2 | 6/2003 | Bourdon |
| 6,575,163 B1 | 6/2003 | Berthon-Jones |
| 6,578,575 B1 | 6/2003 | Jonson |
| 6,581,597 B2 | 6/2003 | Sugiura |
| 6,588,422 B1 | 7/2003 | Berthon-Jones et al. |
| 6,595,213 B2 | 7/2003 | Bennarsten |
| 6,609,517 B1 | 8/2003 | Estes et al. |
| 6,612,995 B2 | 9/2003 | Leonhardt et al. |
| 6,622,726 B1 | 9/2003 | Du |
| 6,626,175 B2 | 9/2003 | Jafari et al. |
| 6,629,527 B1 | 10/2003 | Estes et al. |
| 6,629,934 B2 | 10/2003 | Mault et al. |
| 6,631,716 B1 | 10/2003 | Robinson et al. |
| 6,640,806 B2 | 11/2003 | Yurko |
| 6,644,310 B1 | 11/2003 | Delache et al. |
| 6,651,657 B1 | 11/2003 | Manigel et al. |
| 6,668,824 B1 | 12/2003 | Isaza et al. |
| 6,672,300 B1 | 1/2004 | Grant |
| 6,675,797 B1 | 1/2004 | Berthon-Jones |
| 6,675,801 B2 | 1/2004 | Wallace et al. |
| 6,679,258 B1 | 1/2004 | Strom |
| 6,688,307 B2 | 2/2004 | Berthon-Jones |
| 6,708,691 B1 | 3/2004 | Hayek |
| 6,718,974 B1 | 4/2004 | Moberg |
| 6,725,447 B1 | 4/2004 | Gilman et al. |
| 6,739,337 B2 | 5/2004 | Isaza |
| 6,755,193 B2 | 6/2004 | Berthon-Jones et al. |
| 6,758,217 B1 | 7/2004 | Younes |
| 6,761,167 B1 | 7/2004 | Nadjafizadeh et al. |
| 6,761,168 B1 | 7/2004 | Nadjafizadeh et al. |
| 6,796,305 B1 | 9/2004 | Banner et al. |
| 6,810,876 B2 | 11/2004 | Berthon-Jones |
| 6,814,074 B1 | 11/2004 | Nadjafizadeh et al. |
| 6,823,866 B2 | 11/2004 | Jafari et al. |
| 6,837,242 B2 | 1/2005 | Younes |
| 6,837,244 B2 | 1/2005 | Yagi et al. |
| 6,854,462 B2 | 2/2005 | Berthon-Jones et al. |
| 6,860,858 B2 | 3/2005 | Green et al. |
| 6,866,040 B1 | 3/2005 | Bourdon |
| 6,877,511 B2 | 4/2005 | DeVries et al. |
| 6,899,103 B1 | 5/2005 | Hood et al. |
| 6,910,480 B1 | 6/2005 | Berthon-Jones |
| 6,915,803 B2 | 7/2005 | Berthon-Jones et al. |
| 6,920,878 B2 | 7/2005 | Sinderby et al. |
| 6,932,084 B2 | 8/2005 | Estes et al. |
| 6,948,497 B2 | 9/2005 | Zdrojkowski et al. |
| 6,960,854 B2 | 11/2005 | Nadjafizadeh et al. |
| 6,976,487 B1 | 12/2005 | Melker et al. |
| 6,997,881 B2 | 2/2006 | Green et al. |
| 7,000,610 B2 | 2/2006 | Bennarsten et al. |
| 7,000,612 B2 | 2/2006 | Jafari et al. |
| 7,013,892 B2 | 3/2006 | Estes et al. |
| 7,021,310 B1 | 4/2006 | Sinderby et al. |
| 7,032,589 B2 | 4/2006 | Kerechanin, II et al. |
| 7,036,504 B2 | 5/2006 | Wallace et al. |
| 7,040,321 B2 | 5/2006 | Göbel |
| 7,055,522 B2 | 6/2006 | Berthon-Jones |
| 7,066,173 B2 | 6/2006 | Banner et al. |
| 7,077,131 B2 | 7/2006 | Hansen |
| 7,096,866 B2 | 8/2006 | Be'eri et al. |
| 7,100,607 B2 | 9/2006 | Zdrojkowski et al. |
| 7,100,609 B2 | 9/2006 | Berthon-Jones et al. |
| 7,117,438 B2 | 10/2006 | Wallace et al. |
| 7,137,389 B2 | 11/2006 | Berthon-Jones |
| 7,152,598 B2 | 12/2006 | Morris et al. |
| 7,162,296 B2 | 1/2007 | Leonhardt et al. |
| 7,210,478 B2 | 5/2007 | Banner et al. |
| 7,225,013 B2 | 5/2007 | Geva et al. |
| 7,246,618 B2 | 7/2007 | Habashi |
| 7,255,103 B2 | 8/2007 | Bassin |
| 7,267,121 B2 | 9/2007 | Ivri |
| 7,270,126 B2 | 9/2007 | Wallace et al. |
| 7,270,128 B2 | 9/2007 | Berthon-Jones et al. |
| 7,296,573 B2 | 11/2007 | Estes et al. |
| 7,305,987 B2 | 12/2007 | Schöller et al. |
| 7,320,320 B2 | 1/2008 | Berthon-Jones |
| 7,334,578 B2 | 2/2008 | Biondi et al. |
| 7,367,337 B2 | 5/2008 | Berthon-Jones et al. |
| 7,369,757 B2 | 5/2008 | Farbarik |
| 7,370,650 B2 | 5/2008 | Nadjafizadeh et al. |
| 7,428,902 B2 | 9/2008 | Du et al. |
| 7,439,856 B2 | 10/2008 | Weiner et al. |
| 7,455,717 B2 | 11/2008 | Sprinkle |
| 7,460,959 B2 | 12/2008 | Jafari |
| 7,475,685 B2 | 1/2009 | Dietz et al. |
| 7,484,508 B2 | 2/2009 | Younes |
| 7,487,773 B2 | 2/2009 | Li |
| 7,509,957 B2 | 3/2009 | Duquette et al. |
| 7,516,742 B2 | 4/2009 | Stenzler et al. |
| 7,520,279 B2 | 4/2009 | Berthon-Jones |
| 7,533,670 B1 | 5/2009 | Freitag et al. |
| 7,556,038 B2 | 7/2009 | Kirby et al. |
| 7,588,031 B2 | 9/2009 | Truschel et al. |
| 7,610,914 B2 | 11/2009 | Bolam et al. |
| 7,617,824 B2 | 11/2009 | Doyle |
| 7,621,270 B2 | 11/2009 | Morris et al. |
| 7,621,271 B2 | 11/2009 | Brugnoli |
| 7,644,713 B2 | 1/2010 | Berthon-Jones |
| 7,654,802 B2 | 2/2010 | Crawford, Jr. et al. |
| 7,672,720 B2 | 3/2010 | Heath |
| 7,678,058 B2 | 3/2010 | Patangay et al. |
| 7,678,061 B2 | 3/2010 | Lee et al. |
| 7,682,312 B2 | 3/2010 | Lurie |
| 7,690,378 B1 | 4/2010 | Turcott |
| 7,694,677 B2 | 4/2010 | Tang |
| 7,697,990 B2 | 4/2010 | Ujhazy et al. |
| 7,708,016 B2 | 5/2010 | Zaiser et al. |

(56) References Cited

U.S. PATENT DOCUMENTS

| | | |
|---|---|---|
| 7,717,110 B2 | 5/2010 | Kane et al. |
| 7,717,111 B2 | 5/2010 | Schneider et al. |
| 7,717,113 B2 | 5/2010 | Andrieux |
| 7,722,546 B2 | 5/2010 | Madaus et al. |
| D618,356 S | 6/2010 | Ross |
| 7,727,160 B2 | 6/2010 | Green et al. |
| 7,730,886 B2 | 6/2010 | Berthon-Jones |
| 7,751,894 B1 | 7/2010 | Freeberg |
| 7,763,097 B2 | 7/2010 | Federspiel et al. |
| 7,770,578 B2 | 8/2010 | Estes et al. |
| 7,784,461 B2 | 8/2010 | Figueiredo et al. |
| 7,793,659 B2 | 9/2010 | Breen |
| 7,802,571 B2 | 9/2010 | Tehrani |
| 7,810,496 B2 | 10/2010 | Estes et al. |
| 7,810,497 B2 | 10/2010 | Pittman et al. |
| 7,819,815 B2 | 10/2010 | Younes |
| 7,823,588 B2 | 11/2010 | Hansen |
| 7,849,854 B2 | 12/2010 | DeVries et al. |
| 7,855,716 B2 | 12/2010 | McCreary et al. |
| 7,866,318 B2 | 1/2011 | Bassin |
| 7,874,293 B2 | 1/2011 | Gunaratnam et al. |
| D632,796 S | 2/2011 | Ross et al. |
| D632,797 S | 2/2011 | Ross et al. |
| 7,891,354 B2 | 2/2011 | Farbarik |
| 7,893,560 B2 | 2/2011 | Carter |
| 7,914,459 B2 | 3/2011 | Green et al. |
| D638,852 S | 5/2011 | Skidmore et al. |
| 7,934,499 B2 | 5/2011 | Berthon-Jones |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 9,358,355 B2 | 6/2016 | Graboi et al. |
| 10,639,441 B2 | 5/2020 | Graboi |
| 2002/0013517 A1 | 1/2002 | West et al. |
| 2002/0183979 A1 | 12/2002 | Wildman |
| 2005/0035862 A1 | 2/2005 | Wildman |
| 2005/0039748 A1 | 2/2005 | Andrieux |
| 2005/0139212 A1 | 6/2005 | Bourdon |
| 2006/0155336 A1 | 7/2006 | Heath |
| 2006/0174884 A1 | 8/2006 | Habashi |
| 2006/0235324 A1 | 10/2006 | Lynn |
| 2006/0249148 A1 | 11/2006 | Younes |
| 2006/0278223 A1 | 12/2006 | Younes |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0044796 A1 | 3/2007 | Zdrojkowski et al. |
| 2007/0044799 A1 | 3/2007 | Hete et al. |
| 2007/0077200 A1 | 4/2007 | Baker |
| 2007/0215146 A1 | 9/2007 | Douglas et al. |
| 2007/0227537 A1 | 10/2007 | Bemister et al. |
| 2007/0272241 A1 | 11/2007 | Sanborn et al. |
| 2007/0284361 A1 | 12/2007 | Nadjafizadeh et al. |
| 2008/0011301 A1 | 1/2008 | Qian |
| 2008/0017198 A1 | 1/2008 | Ivri |
| 2008/0041380 A1 | 2/2008 | Wallace et al. |
| 2008/0045813 A1 | 2/2008 | Phuah et al. |
| 2008/0053441 A1 | 3/2008 | Gottlib et al. |
| 2008/0053443 A1 | 3/2008 | Estes et al. |
| 2008/0053444 A1 | 3/2008 | Estes et al. |
| 2008/0072896 A1 | 3/2008 | Setzer et al. |
| 2008/0072901 A1 | 3/2008 | Habashi |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0092894 A1 | 4/2008 | Nicolazzi et al. |
| 2008/0097234 A1 | 4/2008 | Nicolazzi et al. |
| 2008/0110461 A1 | 5/2008 | Mulqueeny et al. |
| 2008/0142012 A1 | 6/2008 | Farnsworth et al. |
| 2008/0163872 A1 | 7/2008 | Negele et al. |
| 2008/0185002 A1 | 8/2008 | Berthon-Jones et al. |
| 2008/0196720 A1 | 8/2008 | Kollmeyer et al. |
| 2008/0202528 A1 | 8/2008 | Carter et al. |
| 2008/0216832 A1 | 9/2008 | Carter et al. |
| 2008/0216833 A1 | 9/2008 | Pujol et al. |
| 2008/0234595 A1 | 9/2008 | Ranieri et al. |
| 2008/0257349 A1 | 10/2008 | Hedner et al. |
| 2008/0283061 A1 | 11/2008 | Tiedje |
| 2008/0295839 A1 | 12/2008 | Habashi |
| 2008/0302363 A1 | 12/2008 | Kroupa |
| 2009/0020120 A1 | 1/2009 | Schatzl et al. |
| 2009/0038616 A1 | 2/2009 | Mulcahy et al. |
| 2009/0056719 A1 | 3/2009 | Newman, Jr. |
| 2009/0084381 A1 | 4/2009 | DeVries et al. |
| 2009/0095298 A1 | 4/2009 | Gunaratnam et al. |
| 2009/0107502 A1 | 4/2009 | Younes |
| 2009/0114224 A1 | 5/2009 | Handzsuj et al. |
| 2009/0159082 A1 | 6/2009 | Eger |
| 2009/0165795 A1 | 7/2009 | Nadjafizadeh et al. |
| 2009/0171176 A1 | 7/2009 | Andersohn |
| 2009/0173347 A1 | 7/2009 | Berthon-Jones |
| 2009/0188502 A1 | 7/2009 | Tiedje |
| 2009/0199855 A1 | 8/2009 | Davenport |
| 2009/0205661 A1 | 8/2009 | Stephenson et al. |
| 2009/0205663 A1 | 8/2009 | Vandine et al. |
| 2009/0221926 A1 | 9/2009 | Younes |
| 2009/0229611 A1 | 9/2009 | Martin et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0247891 A1 | 10/2009 | Wood |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2009/0313046 A1 | 12/2009 | Badgett et al. |
| 2010/0001838 A1 | 1/2010 | Miodownik et al. |
| 2010/0011307 A1 | 1/2010 | Desfossez et al. |
| 2010/0024820 A1 | 2/2010 | Bourdon |
| 2010/0051026 A1 | 3/2010 | Graboi |
| 2010/0051029 A1 | 3/2010 | Jafari et al. |
| 2010/0065055 A1 | 3/2010 | Morris et al. |
| 2010/0065057 A1 | 3/2010 | Berthon-Jones |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0137380 A1 | 6/2010 | Maybaum |
| 2010/0137723 A1 | 6/2010 | Patangay et al. |
| 2010/0137729 A1 | 6/2010 | Pierry et al. |
| 2010/0137730 A1 | 6/2010 | Hatlestad |
| 2010/0139660 A1 | 6/2010 | Adahan |
| 2010/0145201 A1 | 6/2010 | Westbrook et al. |

(56) References Cited

U.S. PATENT DOCUMENTS

| | | |
|---|---|---|
| 2010/0147303 A1 | 6/2010 | Jafari et al. |
| 2010/0152553 A1 | 6/2010 | Ujhazy et al. |
| 2010/0152560 A1 | 6/2010 | Turcott |
| 2010/0170512 A1 | 7/2010 | Kuypers et al. |
| 2010/0174200 A1 | 7/2010 | Wood et al. |
| 2010/0174207 A1 | 7/2010 | Lee et al. |
| 2010/0180898 A1 | 7/2010 | Schneider et al. |
| 2010/0186741 A1 | 7/2010 | Aylsworth et al. |
| 2010/0186742 A1 | 7/2010 | Sherman et al. |
| 2010/0186743 A1 | 7/2010 | Kane et al. |
| 2010/0186744 A1 | 7/2010 | Andrieux |
| 2010/0191076 A1 | 7/2010 | Lewicke et al. |
| 2010/0191137 A1 | 7/2010 | Brada et al. |
| 2010/0192094 A1 | 7/2010 | Jeha et al. |
| 2010/0198086 A1 | 8/2010 | Kuo et al. |
| 2010/0199991 A1 | 8/2010 | Koledin |
| 2010/0210924 A1 | 8/2010 | Parthasarathy et al. |
| 2010/0218764 A1 | 9/2010 | Kwok et al. |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0218773 A1 | 9/2010 | Thornton |
| 2010/0222692 A1 | 9/2010 | McCawley et al. |
| 2010/0224190 A1 | 9/2010 | Tilley et al. |
| 2010/0228133 A1 | 9/2010 | Averina et al. |
| 2010/0228134 A1 | 9/2010 | Martikka et al. |
| 2010/0229863 A1 | 9/2010 | Enk |
| 2010/0234750 A1 | 9/2010 | Ariav et al. |
| 2010/0236553 A1 | 9/2010 | Jafari et al. |
| 2010/0236554 A1 | 9/2010 | Prete |
| 2010/0236555 A1 | 9/2010 | Jafari et al. |
| 2010/0241009 A1 | 9/2010 | Petkie |
| 2010/0242961 A1 | 9/2010 | Mougel et al. |
| 2010/0242965 A1 | 9/2010 | Berthon-Jones |
| 2010/0249630 A1 | 9/2010 | Droitcour et al. |
| 2010/0249631 A1 | 9/2010 | Aoki et al. |
| 2010/0249632 A1 | 9/2010 | Lee et al. |
| 2010/0249633 A1 | 9/2010 | Droitcour et al. |
| 2010/0252037 A1 | 10/2010 | Wondka et al. |
| 2010/0252039 A1 | 10/2010 | Cipollone et al. |
| 2010/0252040 A1 | 10/2010 | Kapust et al. |
| 2010/0252041 A1 | 10/2010 | Kapust et al. |
| 2010/0252042 A1 | 10/2010 | Kapust et al. |
| 2010/0252043 A1 | 10/2010 | Freitag |
| 2010/0256463 A1 | 10/2010 | Greenwald et al. |
| 2010/0258116 A1 | 10/2010 | Federspiel et al. |
| 2010/0258124 A1 | 10/2010 | Madaus et al. |
| 2010/0258126 A1 | 10/2010 | Ujhazy et al. |
| 2010/0258127 A1 | 10/2010 | Hk |
| 2010/0262032 A1 | 10/2010 | Freeberg |
| 2010/0275920 A1 | 11/2010 | Tham et al. |
| 2010/0282259 A1 | 11/2010 | Figueiredo et al. |
| 2010/0288279 A1 | 11/2010 | Seiver et al. |
| 2010/0288283 A1 | 11/2010 | Campbell et al. |
| 2010/0292544 A1 | 11/2010 | Sherman et al. |
| 2010/0300446 A1 | 12/2010 | Nicolazzi et al. |
| 2011/0011400 A1 | 1/2011 | Gentner et al. |
| 2011/0017214 A1 | 1/2011 | Tehrani |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0036352 A1 | 2/2011 | Estes et al. |
| 2011/0041849 A1 | 2/2011 | Chen et al. |
| 2011/0041850 A1 | 2/2011 | Vandine et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1 | 6/2011 | Winter et al. |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |

(56) References Cited

U.S. PATENT DOCUMENTS

| | | |
|---|---|---|
| 2013/0199534 A1 | 8/2013 | Steinhauer et al. |
| 2014/0251328 A1 | 9/2014 | Graboi et al. |
| 2016/0256643 A1 | 9/2016 | Graboi et al. |

FOREIGN PATENT DOCUMENTS

| | | |
|---|---|---|
| EP | 858352 | 1/2005 |
| EP | 1515767 | 8/2009 |
| WO | WO 9014852 | 12/1990 |
| WO | WO 9214505 | 9/1992 |
| WO | WO 9308857 | 5/1993 |
| WO | WO 199715343 | 5/1997 |
| WO | WO 9812965 | 4/1998 |
| WO | WO 199951292 | 10/1999 |
| WO | WO 199962580 | 12/1999 |
| WO | WO 2000/10634 | 3/2000 |
| WO | WO 200078380 | 12/2000 |
| WO | WO 01/00264 | 1/2001 |
| WO | WO 01/00265 | 1/2001 |
| WO | WO 200174430 | 10/2001 |
| WO | WO 2002028460 | 4/2002 |
| WO | WO 2002032488 | 4/2002 |
| WO | WO 2003008027 | 1/2003 |
| WO | WO 04047621 | 6/2004 |
| WO | WO 2005004780 | 1/2005 |
| WO | WO 2007102866 | 9/2007 |
| WO | WO 2007145948 | 12/2007 |

OTHER PUBLICATIONS

7200 Ventilatory System: Addendum/Errata. Nellcor Puritan Bennett, Part No. 4-023576-00, Rev. A, Apr. 1998, pp. 1-32.
800 Operator's and Technical Reference Manual. Series Ventilator System, Nellcor Puritan Bennett, Part No. 4-070088-00, Rev. L, Aug. 2010, pp. 1-476.
840 Operator's and Technical Reference Manual. Ventilator System, Nellcor Puritan Bennett, Part No. 4-075609-00, Rev. G, Oct. 2006, pp. 1-424.
Puritan Bennett 980 Series Ventilator Operator's Manual, Covidien, Jan. 29, 2014, Part. No. 10077893 A 2014-01, 506 pages.

Unsafe to move
Disconnect:
- Prox sensor
- Vent circuit
- Oximeter

Unsafe to move

Disconnect:

- Prox sensor ☒
- Vent circuit ☒
- Oximeter ☒
- Capnometer sensor ☒
- ET tube cuff ☒
- Catheter ☐
- Carinal pressure tube ☒
- ECG Leads ☒
- Esophageal balloon ☒
- Intra-cranial pressure monitor ☒
- Infusion pump ☒
- Chest tube ☐
- Intra-aortic balloon pump ☒
- Nasogastric tube ☒

FIG. 5

Safe to move

- Prox sensor ☒
- Vent circuit ☒
- Oximeter ☒
- Capnometer sensor ☒
- ET tube cuff ☒
- Catheter ☒
- Carinal pressure tube ☒
- ECG Leads ☒
- Esophageal balloon ☒
- Intra-cranial pressure monitor ☒
- Infusion pump ☒
- Chest tube ☒
- Intra-aortic balloon pump ☒
- Nasogastric tube ☒

Not Connected

Reconnect:
- Prox sensor
- Vent circuit
- Oximeter

FIG. 7

METHODS AND SYSTEMS FOR MANAGING A PATIENT MOVE

CROSS-REFERENCE TO RELATED APPLICATIONS

This application is a continuation application of U.S. patent application Ser. No. 15/155,595, entitled "METHODS AND SYSTEMS FOR MANAGING A PATIENT MOVE," filed on May 16, 2016, which application is a divisional application of U.S. patent application Ser. No. 13/793,981 (now U.S. Pat. No. 9,358,355), filed on Mar. 11, 2013, the entire disclosures of which are hereby incorporated herein by reference. Priority is claimed to the above applications.

INTRODUCTION

Medical ventilator systems have long been used to provide supplemental oxygen/ventilatory support to patients. These ventilators typically comprise a source of pressurized air and oxygen which is fluidly connected to the patient through a conduit. Ventilators are adapted to improve safety and patient comfort. For example, some ventilators have been adapted to monitor the patient to ensure that the patient is being properly ventilated. As ventilators advance by integrating and/or connecting to other devices, the number of hoses and cables attached to the ventilators also increases.

MANAGING A PATIENT MOVE

This disclosure describes systems and methods for managing a move of a patient being monitored or treated by a medical system, such as a medical ventilator. The disclosure describes a novel approach for preventing a patient that is connected to a monitoring and/or treatment system from being moved from a first location to second different location, before all of the necessary hoses have been disconnected from the patient. Further, the disclosure describes a novel approach of ensuring that all of the necessary hoses are reconnected to a patient being monitored or treated by a monitoring and/or treatment system after being moved from the first location to the second different location.

In part, this disclosure describes a method for managing a move of a patient connected to a medical ventilator system. The method including:

receiving a movement notice of an intended patient move from a first location to a second location, wherein the first location and the second location are not the same;

determining a disconnection status of each necessary hose based on the notice; and issuing a movement notification based on the determined disconnection statuses.

Yet another aspect of this disclosure describes a medical ventilator system including a pressure generating system, a plurality of sensors operatively coupled to at least one of the pressure generating system, the patient, and the ventilator breathing circuit, an operator interface, a movement module, a status module, a notification module, and a display module. The pressure generating system is adapted to control a flow of gas from a gas supply to a patient via a ventilator breathing circuit. The plurality of sensors monitors a plurality of parameters to generate sensor output. The operator interface receives operator input. The movement module determines an intended patient move from a first location to a second location based on at least one of the sensor output and operator input. The first location and the second location are not the same. The status module in response to the determined intended patient move determines a disconnection status of each necessary hose based on at least one of the sensor output and the operator input. The notification module determines a movement notification based the disconnection statuses from the status module. The display module displays the movement notification.

The disclosure further describes a computer-readable medium having computer-executable instructions for performing a method for managing a move of a patient connected to a medical ventilator system. The method includes:

repeatedly receiving a movement notice of an intended patient move from a first location to a second location, wherein the first location and the second location are not the same;

repeatedly determining a disconnection status of each necessary hose based on the notice; and repeatedly issuing a movement notification based on the determined disconnection statuses.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the disclosure and the claims.

BRIEF DESCRIPTION OF THE DRAWINGS

The following drawing figures, which form a part of this application, are illustrative of embodiments, systems, and methods described below and are not meant to limit the scope of the disclosure in any manner, which scope shall be based on the claims appended hereto.

FIG. 5 illustrates an embodiment of a movement notification.

FIG. 6 illustrates an embodiment of a movement notification.

FIG. 7 illustrates an embodiment of a reconnection notification.

DETAILED DESCRIPTION

Although the techniques introduced above and discussed in detail below may be implemented for a variety of medical devices, the present disclosure will discuss the implementation of these techniques in the context of a medical ventilator for use in providing ventilation support to a human patient. The reader will understand that the technology described also applies to other medical systems or devices that have multiple patient connections, such as vital signs monitoring devices, intra-aortic balloon pumps, pulse oximeters, infusion pumps, and etc. Additionally, these medical systems or devices could also be adapted for non-human patients and patient transport systems.

Over the years, the number of hoses and cable connected from medical systems, such as ventilators, to a patient has increased. While "cables" and "hoses" have different definitions, these terms are utilized interchangeably herein as a component that connects to a patient with each term being inclusive of the other. In order to move a patient, some or all of the hoses and cables connected from the medical system or device to the patient have to be disconnected from the patient. Accordingly, there may be a number of hoses and cables to disconnect from the patient before a patient can be moved away from the medical system. Because of the large number of hoses that need to be disconnected, a clinician could easily forget to disconnect one or more of the hoses before moving the patient and could potentially endanger the patient. For example, the movement could cause a patient to become extubated. Additionally, the operator or clinician after moving a patient may forget to reconnect a necessary hose or tube, which could also endanger the patient.

The present disclosure describes systems and methods for managing the move a patient to prevent the move of a patient without the disconnection of all the necessary hoses. In some embodiments, the systems and methods described herein issue a movement notification to inform the operator if the patient is ready for movement. In further embodiments, the systems and method the systems and methods described herein issue a reconnection notification to inform the operator that all of the necessary hoses have been reconnected to the patient after the patient has been move from one location to another location.

Figure 1:
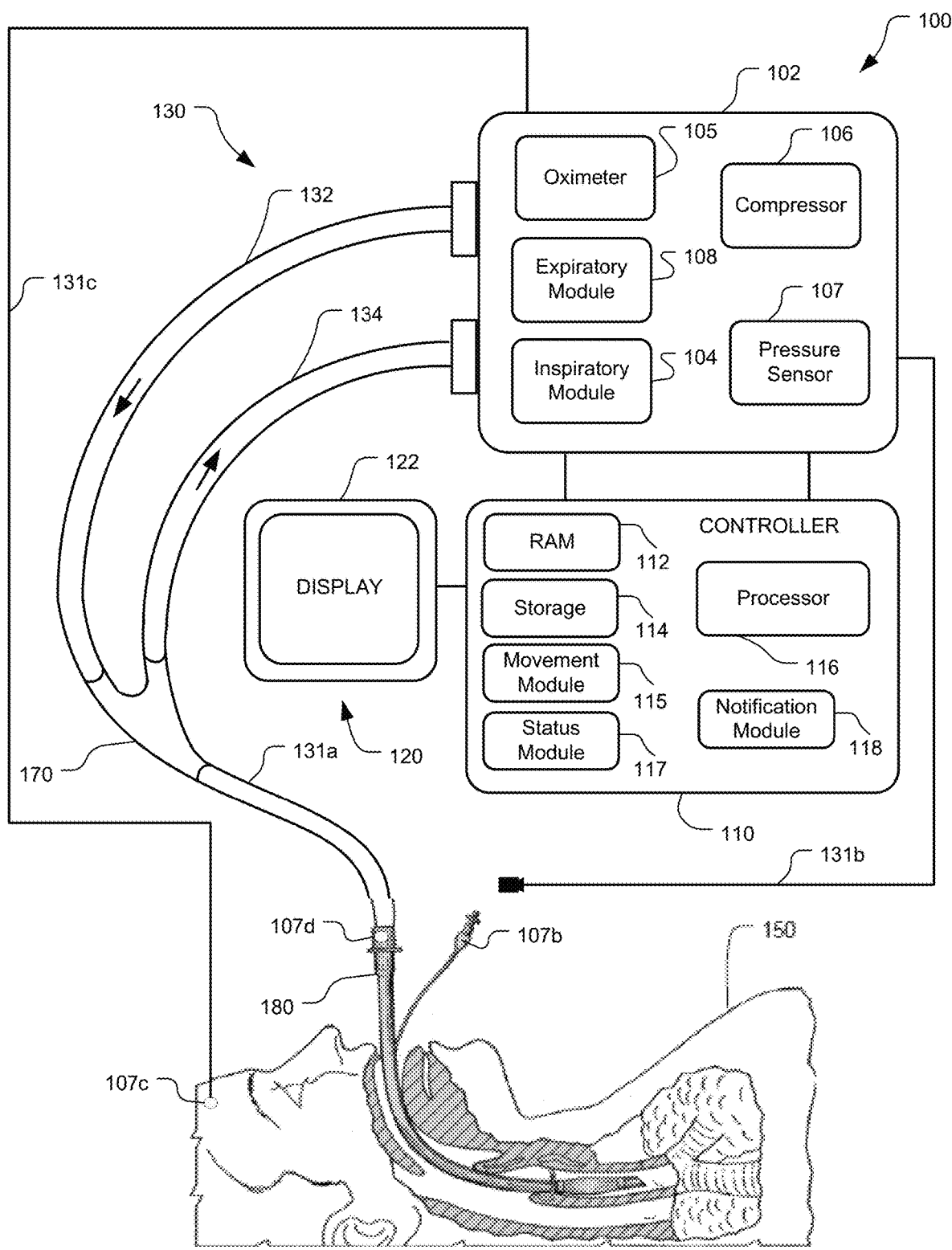
FIG. 1 illustrates an embodiment of a ventilator system connected to a human patient.

FIG. 1 is a diagram illustrating an embodiment of an exemplary ventilator 100 connected to a human patient 150. Ventilator 100 includes a pneumatic gas delivery system 102 (also referred to as a pressure generating system 102 or pneumatic system 102) for circulating breathing gases to and from patient 150 via the ventilation tubing system 130, which couples the patient 150 to the pneumatic system 102 via an invasive (e.g., endotracheal tube, as shown) or a non-invasive (e.g., nasal mask) patient interface 180.

Ventilation tubing system 130 (or patient circuit 130 or breathing circuit 130) may be a two-limb (shown) or a one-limb circuit for carrying gases to and from the patient 150. In a two-limb embodiment, a fitting, typically referred to as a "wye-fitting" 170, may be provided to couple a patient interface 180 (as shown, an endotracheal tube) to an inspiratory limb 132 and an expiratory limb 134 of the ventilation tubing system 130.

Pneumatic system 102 may be configured in a variety of ways. In the present example, pneumatic system 102 includes an expiratory module 108 coupled with the expiratory limb 134 and an inspiratory module 104 coupled with the inspiratory limb 132. Compressor 106 or other source(s) of pressurized gases (e.g., air, oxygen, and/or helium) is coupled with inspiratory module 104 and the expiratory module 108 to provide a gas source for ventilatory support via inspiratory limb 132.

The inspiratory module 104 is configured to deliver gases to the patient 150 according to prescribed ventilatory settings. The expiratory module 108 is configured to release gases from the patient's lungs according to prescribed ventilatory settings. Specifically, expiratory module 108 is associated with and/or controls an expiratory valve for releasing gases from the patient 150.

The ventilator 100 may also include one or more sensors 107 communicatively coupled to ventilator 100 and/or patient 150. The sensors 107 may be located in the pneumatic system 102, ventilation tubing system 130, and/or on the patient 150. The embodiment of FIG. 1 illustrates a sensor 107 in pneumatic system 102, in the patient interface 180, and attached to the patient 150.

Sensors 107 may communicate with various components of ventilator 100, e.g., pneumatic system 102, other sensors 107, processor 116, movement module 115, status module 117, notification module 118 and/or any other suitable components and/or modules. In one embodiment, sensors 107 generate output and send this output to pneumatic system 102, other sensors 107, processor 116, movement module 115, status module 117, notification module 118 and/or any other suitable components and/or modules. Sensors 107 may employ any suitable sensory or derivative technique for monitoring one or more parameters associated with the patient 150 and the ventilation of a patient 150. Sensors 107 may detect changes in patient parameters indicative of patient triggering, for example. Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, FIG. 1 illustrates a pressure sensor 107a, an endotracheal tube pressure sensor connection 107b, an oximeter sensor 107c, and a sensor 107d, which may be any one of the following sensors: a proximity tag 107d, a motion sensor 107d, or a RFID tag 107d. In some embodiments, a sensor 107 may be wireless as illustrated by sensor 107d in FIG. 1. Further, sensors 107 may detect where a hose or tube is connected to a patient 150 and/or a ventilator 100. In some examples, sensors 107 may be affixed to the ventilatory tubing or may be embedded in the tubing itself. In other embodiments, sensors 107 may detect patient and/or ventilator movement. For example, the ventilator 100 may be electronically coupled to a motion sensor 107d, a proximity tag 107d, RFID tag 107d and/or any other sensor 107 suitable for determining movement of the patient 150 and/or ventilator 100. Any sensory device useful for monitoring changes in measurable parameters during ventilatory treatment, patient location, or the connection status of a hose or cable may be employed in accordance with embodiments described herein.

As should be appreciated, with reference to the Equation of Motion, ventilatory parameters are highly interrelated and, according to embodiments, may be either directly or indirectly monitored. That is, parameters may be directly monitored by one or more sensors 107, as described above, or may be indirectly monitored or estimated/calculated using a model, such as a model derived from the Equation of Motion (e.g., Target Airway Pressure$(t) = E_g \int Q_P at + Q_P R_g$ − Patient Effort$(t)$).

The pneumatic system 102 may include a variety of other components, including an oximeter 105, mixing modules, valves, tubing, accumulators, filters, etc. Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.).

In one embodiment, the operator interface 120 of the ventilator 100 includes a display module 122 communicatively coupled to ventilator 100. Display module 122 may provide various input screens, for receiving clinician input, and various display screens, for presenting useful information to the clinician. In one embodiment, the display module 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display module 122 and/or or another communication device.

Display module 122 may also provide useful information in the form of various ventilatory data regarding ventilator parameters, patient location, connection status of necessary hoses 131, and/or the physical condition of a patient 150. The useful information may be derived by the ventilator 100, based on data collected by a processor 116, and the useful information may be displayed to the clinician in the form of graphs, wave representations, lists, check lists, pie graphs, text, or other suitable forms of graphic display. For example, patient data may be displayed on the GUI and/or display module 122. In some embodiments, the display module 122 may be remote display module. Additionally or alternatively, useful information and/or ventilator parameters may be communicated to and displayed on an additional remote display module and/or on a remote monitoring system coupled via any suitable means to the ventilator 100, such as a tablet or PC. The remote display module or remote monitoring system are not physically attached to the pneumatic system 102 of the ventilator 100 and may be in the same room or over a mile away from the patient 150 or the pneumatic system 102 of the ventilator 100. In some embodiments, the display module 122 and/or remote monitoring display system displays a movement notification, a confirmation notification, and/or a reconnection notification.

Controller 110 may include memory 112, one or more processors 116, storage 114, and/or other components of the type commonly found in command and control computing devices. Controller 110 may further include a movement module 115, status module 117, and/or a notification module 118 as illustrated in FIG. 1. In alternative embodiments, a movement module 115, status module 117, and/or a notification module 118 may be located in other components of the ventilator 100, such as the pressure generating system 102 (also known as the pneumatic system 102).

The memory 112 includes non-transitory, computer-readable storage media that stores software that is executed by the processor 116 and which controls the operation of the ventilator 100. In an embodiment, the memory 112 includes one or more solid-state storage devices such as flash memory chips. In an alternative embodiment, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

The movement module 115 determines an intended patient move from a first location to a second different location based on sensor output and/or operator input. In some embodiments, the movement module 115 determines an intended patient move based on operator input. For example, the operator may select or input into the ventilator 100 that the patient 150 is going to be moved, such as by selecting or pushing a transport button. In some embodiments, the ventilator 100 determines an intended patient move based on sensor output. For example, the ventilator 100 may be connected to a motion sensor 107d, a proximity tag 107d, a RFID tag 107d and/or any other sensor 107 suitable for determining movement of the patient 150 and/or ventilator 100. In some embodiments, the ventilator 100 determines an intended patient move based on a camera directed at the patient. In other embodiments, the ventilator 100 determines an intended patient move based on sensor output and operator input. For example, the ventilator 100 may detect that the patient 150 is being moved based on sensor output, but not determine an intended patient movement until the detected patient movement is confirmed by operator input.

In some embodiments, the ventilator 100 includes a proximity tag 107d as part of proximity system utilized by the ventilator 100. In this embodiment, the proximity tag 107d is attached to a patient 150 or located on a device or mechanism in close proximity or attached to the patient 150, such as the hospitable bed, oximeter sensor 107c, or endotracheal tube 180. In this embodiment, when the proximity tag 107d is located at a predetermined distance from the ventilator 100, the movement module 115 either sends instructions to issue a confirmation notification or determines an intended patient movement. The confirmation notification notifies the operator that the patient 150 is a predetermined distance from the ventilator 100 and requests operator input to confirm or deny an intended patient movement. A notification as used herein may be any suitable system or method for notifying an operator, such as a visual, audio, and/or other sensory notification (e.g., vibration). For example, the notification may be displayed on the screen, alarm, and/or vibrate in order to notify the operator. Accordingly, a notification may be a visual notification, audio notification, and/or a vibrational notification. In some embodiments, the confirmation notification is a displayed transport button that may be selected or pushed by the operator.

In some embodiments, the ventilator 100 includes a motion sensor 107d. In this embodiment, the motion sensor 107d is attached to a patient 150 or located on a device or mechanism in close proximity or attached to the patient 150, such as the hospitable bed, the ventilator 100, or endotracheal tube. In this embodiment, when the motion sensor 107d detects a predetermined amount of movement, the movement module 115 either sends instructions to issue a confirmation notification or determines an intended patient movement. The confirmation notification notifies the operator that motion was detected and requests operator input to confirm or deny an intended patient movement.

In some embodiments, the ventilator 100 includes a RFID tag 107d as part of an RFID system utilized by the ventilator 100. In this embodiment, the RFID tag 107d is attached to a patient 150 or located on a device or mechanism in close proximity or attached to the patient 150, such as the hospitable bed, or endotracheal tube. In this embodiment, when the RFID tag 107d is located at a predetermined distance from the ventilator 100 or can no longer be detected by the ventilator 100 because the RFID tag 107d is out of signal range, the movement module 115 either sends instructions to issue a confirmation notification or determines an intended patient movement. The confirmation notification notifies the operator that the patient 150 is a predetermined distance from the ventilator 100 and requests operator input to confirm or deny an intended patient movement.

If the operator confirms the intended movement, the movement module 115 determines an intended patient movement. In some embodiments, the operator confirms an intended movement by selecting or pushing a transport button. If the operator denies the intended movement, the movement module 115 does not determine an intended patient movement. If the movement module 115 determines an intended patient move from a first location to a second different location, the movement module 115 sends instructions to the status module 117 to perform a disconnection status check. If the movement module 115 does not determine an intended patient move, then the movement module 115 continues to monitor for an intended patient move and does not send any instructions to the status module 117.

The status module 117 determines a disconnection status of each necessary hose 131 or other patient connection based on sensor output and/or operator input. Accordingly, the status module 117 also determines a connection status of each necessary hose 131 based on sensor output and/or operator input since a hose can only be either connected or disconnected. The status module 117 begins checking or monitoring the disconnection statuses of the necessary hoses 131 after the status module 117 receives instructions from the movement module 115. The necessary hose 131 is any ventilator hose 131 that needs to be or should be disconnected from the patient 150 and/or ventilator 100 in order to move the patient 150. In some embodiments, the ventilator 100 determines the necessary hoses 131. The ventilator 100 may determine the necessary hoses 131 based on sensor output or based on a predetermined list programmed into the ventilator 100. In other embodiments, the necessary hoses 131 are selected or input by the operator. For example, FIG. 1 illustrates three different necessary hoses 131, a ventilation tubing circuit 131a, a flow sensor hose 131b, and an oximeter cable 131c. As illustrated in FIG. 1, the ventilation tubing circuit 131a and the oximeter cable 131c are connected, while the flow sensor hose 131b is disconnected.

The ventilator 100 may determine if a necessary hose 131 is disconnected or connected by monitoring sensor output. In some embodiments, the hose 131 may contain a connection sensor that solely determines if a hose 131 is connected or disconnected from a patient 150. In some embodiments, the ventilator 100 determines hose connection status by monitoring the presence or absence of output of a sensor. For example, the ventilator 100 may determine that a capnometer sensor is attached to a patient 150 if the ventilator 100 is receiving a $CO_2$ output from the capnometer sensor and may determine that a capnometer sensor is disconnected from the patient 150 if the ventilator 100 is not receiving a $CO_2$ output from the capnometer sensor. Table 1 below provides a list of sensor outputs that the ventilator 100 may utilize to determine connection statuses of necessary hoses 131. In some embodiments, more than one sensor output may be utilized or different sensor output may be utilized depending on the ventilator components and sensor to determine the connection status of a necessary hose 131.

TABLE 1

Ventilator Determined Connection Status Based on Sensor Output

| Device | Connected | Disconnected |
| --- | --- | --- |
| Capnometer sensor | Presence of $CO_2$ signal | Loss of $CO_2$ signal |
| Capnometer sensor | Presence of circuit pressure | Loss of circuit pressure |
| Endotracheal tube (ET) cuff pressure | Presence of ET cuff pressure signal | Loss of ET cuff pressure signal |
| Proximal flow sensor | Presence of flow signal | Loss of flow signal |
| Proximal flow sensor | Presence of pressure signals from proximal flow sensor | Loss of pressure signals from proximal flow sensor |
| Catheter | Presence of $E_{di}$ signal | Loss of $E_{di}$ signal |
| Carinal pressure | Presence of Carinal pressure signal | Loss of Carinal pressure signal |
| ECG Leads | Presence of ECG signal | Loss of ECG signal |
| ECG Leads | Presence of respiratory rate signal from ECG leads | Loss of respiratory rate signal from ECG leads |
| Esophageal balloon pressure | Presence of Esophageal balloon pressure signal | Loss of Esophageal balloon pressure signal |
| Pulse Oximeter | Presence of oximeter signal from bedside device | Loss of oximeter signal from bedside device |
| Pulmonary Artery (PA) Catheter | Presence of PA signal | Loss of PA signal |
| Intra-cranial pressure (ICP) monitor | Presence of ICP signal | Loss of ICP signal |
| Intra-aortic Balloon Pump (IABP) | Start IABP device (pump on) | Discontinuance IABP device (pump off) |
| Infusion pump | Start of IV fluid flow (pump on) | Discontinuance of IV fluid flow (pump off) |

In some embodiments, the ventilator 100 may determine if a necessary hose 131 is disconnected or connected by monitoring operator input. The operator can select or input the disconnection of each hose 131 as the operator disconnects the hose 131. The status module 117 may send instructions to the display module 122 to display a disconnection check list to provide the operator with a list of all the necessary hoses 131 that need to be disconnected. In some embodiments, the disconnection check list may be interactive and mark each necessary hose 131 as a hose 131 is disconnected based on operator input.

In other embodiments, the ventilator 100 determines the disconnection statutes based on sensor output and operator input. For example, the ventilator 100 may detect that a necessary hose 131 is disconnected based on sensor output, but may not determine a disconnection until the detected disconnection is confirmed by operator input.

The status module 117 continues to check or update the disconnection statuses of the necessary hoses 131 until the status module 117 receives instructions to stop determining the connection statuses of the necessary hoses 131 from operator input and/or from the notification module 118.

The status module 117 sends the determined disconnection statuses of the necessary hoses 131 to the notification module 118. The notification module 118 determines a movement notification based on the disconnection statuses. The notification module 118 sends instruction to other ventilator components to issue the determined or generated movement notification. In some embodiments, the notification module 118 sends the instructions to the display module 122 for displaying the movement notification. In other embodiments, the notification module 118 sends instructions to the processor 116 or pneumatic system 102 for issuing the movement notifications. The notification module 118 may send the instruction to any suitable component or components of the ventilator 100 for issuing the movement notification.

The movement notification notifies the operator about whether the patient 150 is ready or not ready to be moved from a first location to a second different location based on the disconnection statuses received from the status module 117. For example, the patient may be being moved from one hospital room to another room, from one hospital wing to another wing, or even from a hospital to another location, such as the patient home. The movement notification is any suitable system or method for notifying an operator that the patient 150 either ready or not ready to be moved, such as a visual, audio, and/or other sensory notification (e.g., vibration).

If the notification module 118 determines that any of the necessary hoses 131 are still connected based on the received disconnection statuses, then the notification module 118 determines that the patient 150 is not ready to be moved. If the patient 150 is not ready to be moved, then the notification module 118 generates a movement notification that informs the operator that the patient 150 is not ready to be moved. If the notification module 118 determines that all of the necessary hoses 131 have been disconnected, the notification module 118 determines that the patient 150 is ready to be moved from first location to a different second location. If the patient 150 is ready to be moved, then the notification module 118 generates a movement notification that informs the operator that the patient 150 is ready to be moved.

In some embodiments, the movement notification is displayed. FIGS. 3-6 illustrate different embodiments of screen shots of a movement notification 300, 400, 500, 600 and 700. The displayed movement notification will indicate if the patient 150 is ready to be moved or if the patient 150 is not ready to be moved as illustrated in FIGS. 3-6. In some embodiments, the display notification may list each of the necessary hoses 131 and the disconnection status of each of the necessary hoses 131 as illustrated in FIGS. 5 and 6. The disconnection status may be marked with icons, symbols, colors, animation, and/or any other suitable method for showing that a necessary hose 131 is connected or disconnected. In some embodiments, the notification module 118 continuously updates the movement notification based on the received disconnection status from the status module 117 until each of the necessary hoses 131 has been disconnected and/or until operator input is received that ends the movement notification. In further embodiments, the movement notification may be displayed on a graphical user interface and be interactive with the operator as illustrated in FIGS. 5 and 6. In this embodiment, the operator may be able to select a listed necessary hose 131 and change the connection status of the selected necessary hose 131 to connected and/or disconnected.

Figure 3:
FIG. 3 illustrates an embodiment of a movement notification.
Figure 4:
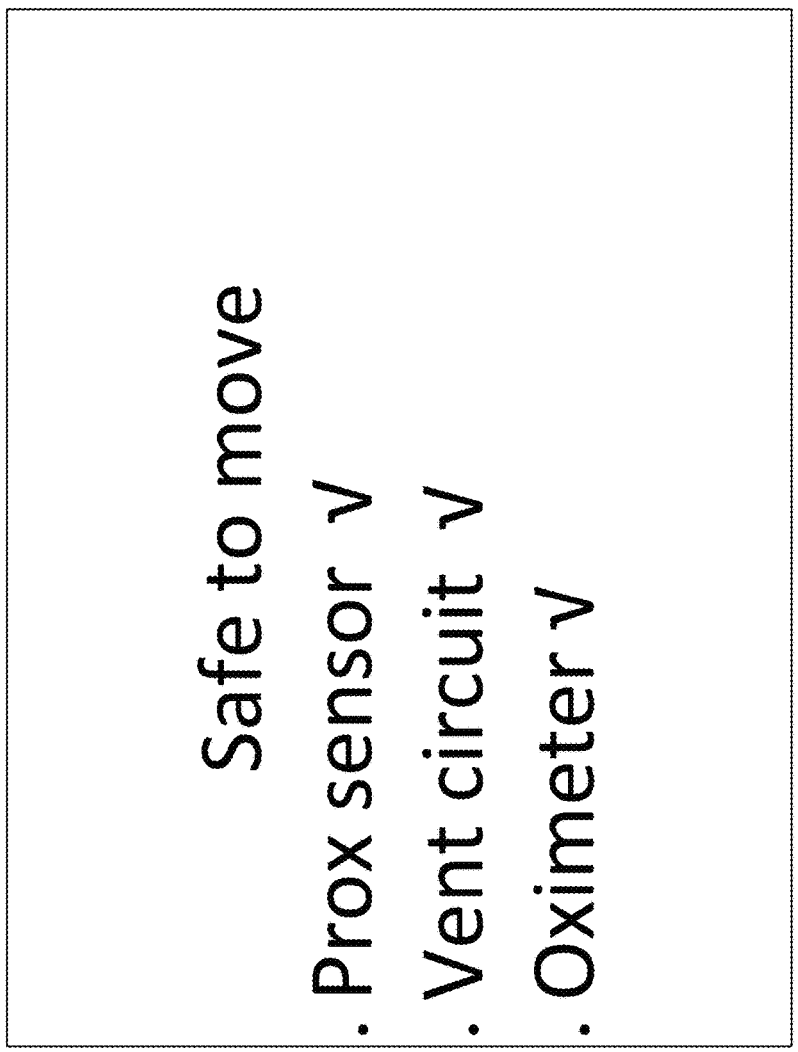
FIG. 4 illustrates an embodiment of a movement notification.

In other embodiments, the displayed movement notification lists only the necessary hoses 131 that are disconnected as illustrated in FIG. 3. In this embodiment, the notification module 118 removes necessary hoses 131 from the movement notification as they become connected based on the disconnection statuses received from status module 117. Accordingly, in this embodiment, if the patient 150 is ready to be moved, then no necessary hoses 131 are listed on the movement notification.

As discussed above, operator input may end the display of the movement notification by the notification module 118. If the operator selects to end the movement notification, the notification module 118 stops sending instruction to the ventilator components for issuing the movement notification. Further, if the operator selects to end the movement notification, the statuses module stops checking or monitoring the connection statuses of the necessary hoses 131. Alternatively, the movement notification may end after the issuance of or after a set amount of time from the issuance of a movement notification that informs the operator that the patient 150 is ready to be moved.

In some embodiments, after the end of a movement notification, the movement module 115 may further determine that the patient 150 has been moved from the first location to the different second location based on operator input and/or generated sensor output. For example, the operator may select or input into the ventilator 100 that the patient 150 has been moved, such as by selecting or pushing a reconnection button. In some embodiments, the ventilator 100 determines the second location based on sensor output. For example, the ventilator 100 may be connected to a motion sensor 107d, a proximity tag 107d, RFID tag 107d and/or any other sensor 107 suitable for determining movement of the patient 150 and/or ventilator 100. In other embodiments, the ventilator 100 determines an intended patient move based on sensor output and operator input. For example, the ventilator 100 may detect that the patient 150 has moved to the second location based on sensor output, but not determine that the patient 150 has moved until the detected second location is confirmed by operator input.

In some embodiments, the sensors may be able to detect that a patient 150 has moved to a second location because the spot of the second location has been input into the ventilator 100. For example, an RFID sensor in the second location may detect the presence of the RFID tag associated with the patient 107d. In another example, a second proximity tag 107d may be utilized in the second location, therefore, when the ventilator 100 is in range of the second proximity tag 107d, the ventilator 100 knows that the patient 150 has been moved to a second location.

If the ventilator 100 detects that the patient 150 is in the second location, the movement module 115 either sends instructions to issue a check notification or determines an intended patient movement. The check notification notifies the operator that the patient 150 is in the second location and requests operator input to confirm or deny that the patient 150 is in the second location.

If the operator confirms the second location, the movement module 115 determines that the patient 150 is in the second location. In some embodiments, the operator confirms the second location by selecting or pushing a reconnection button. If the operator denies the second location, the movement module 115 does not determine that the patient 150 is in the second location. If the movement module 115 determines that the patient 150 has moved from the first location to the second different location, the movement module 115 sends instructions to the status module 117 to perform a connection status check. If the movement module 115 does not determine that the patient 150 has moved to the second location, then the movement module 115 continues to monitor for the second location and does not send any instructions to the status module 117.

As discussed above, the status module 117 determines a connection status of each necessary hose 131 based on sensor output and/or operator input. Again, the status module 117 begins checking or monitoring the connection statuses of the necessary hoses 131 after the status module 117 receives instructions from the movement module 115. Again, the status module 117 continues to check or update the connection statuses of the necessary hoses 131 until the status module 117 receives instructions to stop determining the connection statuses of the necessary hoses 131 from operator input and/or from the notification module 118. The status module 117 sends the determined connection statuses of the necessary hoses 131 to the notification module 118.

The notification module 118 determines a reconnection notification based on the connection statuses. The reconnection notification notifies the operator about whether the or not all of the necessary hoses 131 have been reconnected to the patient 150 based on the connection statuses received from the status module 117. The reconnection notification is any suitable system or method for notifying an operator that the patient 150 is either properly connected to ventilator 100 for ventilation or not properly connected to the ventilator 100 for ventilation, such as a visual, audio, and/or other sensory notification (e.g., vibration).

The notification module 118 sends instructions to other ventilator 100 components to issue the determined or generated reconnection notification. In some embodiments, the notification module 118 sends the instructions to the display module 122 for displaying the reconnection notification. In other embodiments, the notification module 118 sends instructions to the processor 116 or pneumatic system 102 for issuing the reconnection notification. The notification module 118 may send the instruction to any suitable component or components of the ventilator 100 for issuing the reconnection notification.

If the notification module 118 determines that any of the necessary hoses 131 are not connected to the patient 150 based on the received disconnection statuses, then the notification module 118 determines that the patient 150 is not properly connected to the ventilator 100. If the patient 150 is not properly connected, then the notification module 118 generates a reconnection notification that informs the operator that the patient 150 is not properly connected to the ventilator 100 or that at least one necessary hose 131 still needs to be connected. If the patient 150 is properly connected, then the notification module 118 generates a reconnection notification that informs the operator that the patient 150 is not properly connected to the ventilator 100 or that all of the necessary hoses 131 are connected to the patient 150.

In some embodiments, the reconnection notification is displayed. FIG. 7 illustrates an embodiment of a screen shot of a reconnection notification 700. The displayed reconnection notification will indicate if the all of the necessary hoses 131 have been reconnected to the patient 150 or not. In some embodiments, the displayed reconnection notification may list each of the necessary hoses 131 and the disconnection status of each of the necessary hoses 131. The disconnection status may be marked with icons, symbols, colors, animation, and/or any other suitable method for showing that a necessary hose 131 is connected or disconnected. In some embodiments, the notification module 118 continuously updates the displayed reconnection notification based on the received disconnection status from the status module 117 until each of the necessary hoses 131 has been connected and/or until operator input is received that ends the reconnection notification. In further embodiments, the reconnection notification may be displayed on a graphical user interface and be interactive with the operator. In this embodiment, the operator may be able to select a listed necessary hose 131 and change the connection status of the selected necessary hose 131 to connected and/or disconnected.

In other embodiments, the displayed reconnection notification lists only the necessary hoses 131 that are disconnected as illustrated in FIG. 7. In this embodiment, the notification module 118 removes necessary hoses 131 from the displayed reconnection notification as they become connected based on the disconnection statuses received from status module 117. Accordingly, in this embodiment, if the all of the necessary hoses 131 are connected to the patient 150, then no necessary hoses 131 are listed on the displayed reconnection notification.

As discussed above, operator input may end the display of the reconnection notification by the notification module 118. If the operator selects to end the reconnection notification, the notification module 118 stops sending instructions to the ventilator components for issuing the reconnection notification. Further, if the operator selects to end the reconnection notification, the status module 117 stops checking or monitoring the connection statuses of the necessary hoses 131. Alternatively, the reconnection notification may end after issuance of or after a set amount of time from the issuance of a reconnection notification that informs the operator that the all of the necessary hoses 131 have been connected to the patent.

Figure 2:
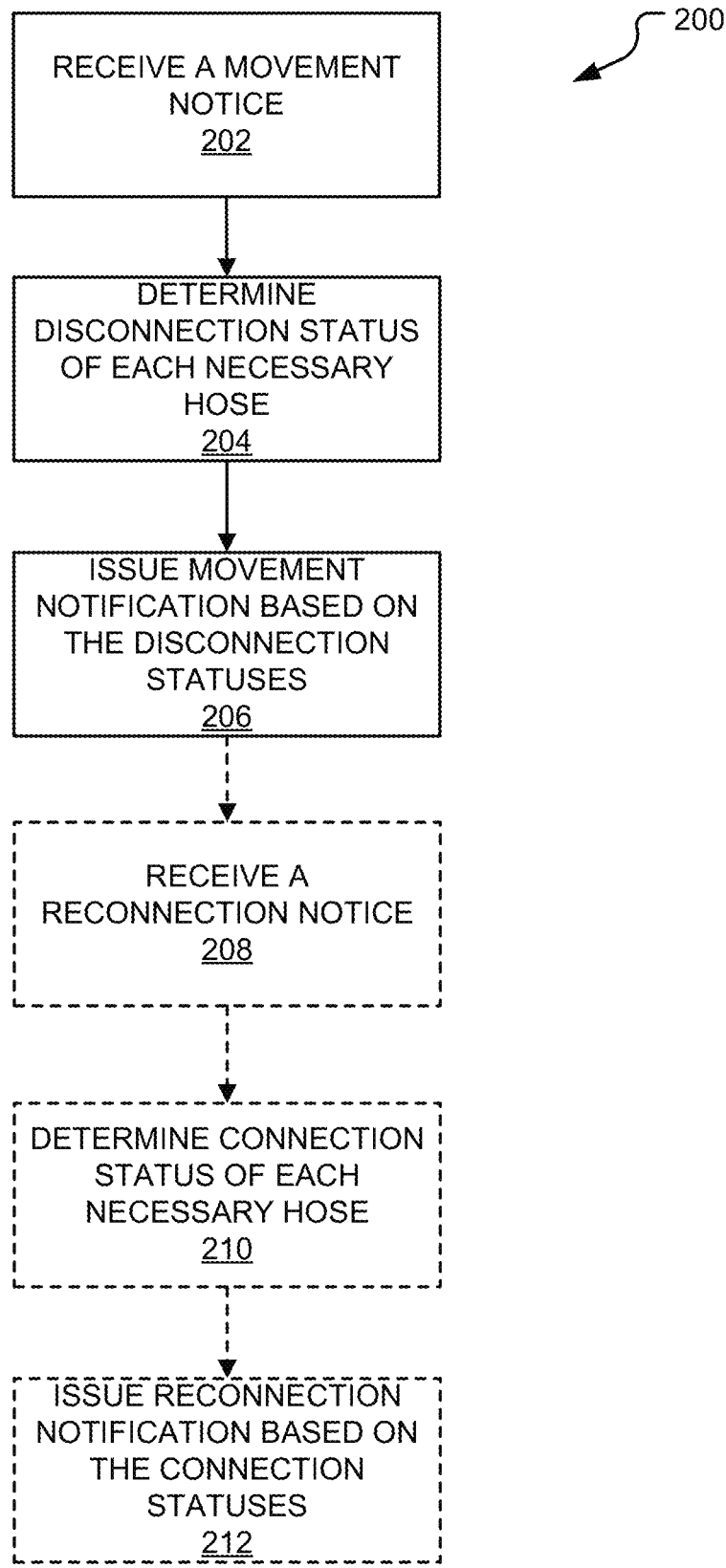
FIG. 2 illustrates an embodiment of a method for managing the move of a patient connected a medical system.

As discussed above, ventilators or medical systems often require numerous hoses to be connected to a patient making it easy for a clinician to forget to disconnect a necessary hose prior to a patient move from a first location to a second location. Accordingly, FIG. 2 illustrates an embodiment of a method 200 for managing a move of a patient connected to a medical system, such as a medical ventilator. More specifically, method 200 ensures that all necessary hoses connected to a patient are disconnected before a patient is moved from a first location to a different second location. Further, in some embodiments, after a patient is moved to the different second location, method 200 also ensures that all of the necessary hoses are reconnected to the patient.

As illustrated, method 200 includes a receiving operation 202. The ventilator or medical system during the receiving operation 202 receives a movement notice. The received movement notice is notice of an intended patient movement from a first location to a second different location. The received movement notice of an intended patient move is based on operator input and/or generated sensor output. For example, the operator may select or input into the medical system that the patient is going to be moved, such as by selecting or pushing a transport button. In some embodiments, the medical system determines an intended patient move based on sensor output. For example, the medical system may be connected to a motion sensor, a proximity tag, RFID tag and/or any other systems or methods suitable for determining movement of the patient and/or medical system. In other embodiments, the medical system determines an intended patient move based on sensor output and operator input. For example, the medical system may detect that the patient is being moved based on sensor output, but not determine an intended patient movement until the detected patient movement is confirmed by operator input.

For example, the medical system during the receiving operation 202 may issue a confirmation notification that notifies the operator that motion was detected and request operator input to confirm or deny an intended patient movement. If the operator confirms the intended movement, the medical system during receiving operation 202 receives a movement notice. In some embodiments, the operator confirms an intended movement by selecting or pushing a transport button. If the operator denies the intended movement, the medical system during the receiving operation 202 does not receive a movement notice.

Further, method 200 includes a determining operation 204. The ventilator or medical system during the determining operation 204 determines the disconnection status of each necessary hose after the movement notice is received. The medical system during the determining operation 204 determines the disconnection status of each of the necessary hoses based on operator input and/or generated sensor output. Accordingly, the medical system during the determining operation 204 also determines a connection status of each necessary hose based on sensor output and/or operator input because a necessary hose can either be connected or disconnected.

The medical system during the determining operation 204 may determine if a necessary hose is disconnected or connected by monitoring sensor output. In some embodiments, the hose may contain a connection sensor that solely determines if a hose is connected or disconnected from a patient. In some embodiments, the medical system during the determining operation 204 determines hose connection status by monitoring the presence or absence of output of a sensor. For example, the medical system may determine that a capnometer sensor is attached to a patient if the medical system is receiving a $CO_2$ output from the capnometer sensor and may determine that a capnometer sensor is disconnected from the patient if the medical system is not receiving a $CO_2$ output from the capnometer sensor. Table 1 above provides a list of sensor outputs that the medical system may utilize to determine connection statuses of necessary hoses. In some embodiments, more than one sensor output may be utilized or different sensor output may be utilized depending on the medical system components and sensor to determine the connection status of a necessary hose.

In some embodiments, the medical system during the determining operation 204 may determine if a necessary hose is disconnected or connected by monitoring operator input. The operator can select or input the disconnection of each hose as the operator disconnects the hose.

In other embodiments, the medical system during the determining operation 204 determines the disconnection statutes based on sensor output and operator input. For example, the medical system may detect that a necessary hose is disconnected based on sensor output, but may not determine a disconnection until the detected disconnection is confirmed by operator input. In some embodiments, the medical system during the determining operation 204 continues to check or update the disconnection statuses of the necessary hoses until the medical system receives instructions to stop determining the disconnection statuses of the necessary hoses from operator input. In other embodiments, the medical system during the determining operation 204 continues to check or update the disconnection statuses of the necessary hoses until movement notification that informs the operator that it is safe to move the patient from a first location to a second location issues.

Method 200 also includes an issuing operation 206. The ventilator or medical system during issuing operation 206 issues a movement notification based on the determined disconnection status for each necessary hose. The medical system during issuing operation 206 determines a movement notification based on the disconnection statuses and issues the generated movement notification. The movement notification notifies the operator about whether the patient is ready or not ready to be moved from a first location to a second different location. The movement notification is any suitable system or method for notifying an operator that the patient either ready or not ready to be moved, such as a visual, audio, and/or other sensory notification (e.g., vibration). In some embodiments, the medical system during issuing operation 206 displays the movement notification.

If the medical system during issuing operation 206 determines that any of the necessary hoses are still connected based on the received disconnection statuses, then the medical system determines that the patient is not ready to be moved even if the operator has indicated that that such disconnections have been performed. If the patient is not ready to be moved, then the medical system during issuing operation 206 generates a movement notification that informs the operator that the patient is not ready to be moved. Thus, the medical system confirms the operator's inputs of disconnection statuses before indicating that the patient is ready to be moved. If the medical system during issuing operation 206 determines that all of the necessary hoses have been disconnected, the medical system determines that the patient is ready to be moved from first location to a different second location. If the patient is ready to be moved, then the medical system during issuing operation 206 generates a movement notification that informs the operator that the patient is ready to be moved.

In some embodiments, the medical system during issuing operation 206 displays the movement notification. FIGS. 3-6 illustrate embodiments of screen shots of a displayed movement notification 300, 400, 500, 600 and 700. The displayed movement notification will indicate if the patient is ready to be moved or if the patient is not ready to be moved as illustrated in FIGS. 3-6. The display of the movement notification is discussed above in further detail.

As discussed above, operator input may end the display of the movement notification by the medical system during issuing operation 206. If the operator selects to end the movement notification, the medical system during issuing operation 206 stops issuing the movement notification. Further, if the operator selects to end the movement notification, the medical system during the determining operation 204 stops checking or monitoring the disconnection statuses of the necessary hoses. Alternatively, the movement notification may end after the issuance of a movement notification or after a set amount of time after the issuance of the movement notification that informs the operator that the patient is ready to be moved.

In some embodiments, after the ending of the issuing operation 206, method 200 further includes a reconnection receiving operation 208, a connection determining operation 210, and a reconnection notification operation 212. The medical system or medical system during the reconnection receiving operation 208 receives a reconnection notice of an intended reconnection of the patient to the medical system or medical system. The medical system during the reconnection receiving operation 208 receives a reconnection notice based on operator input and/or generated sensor output. For example, the operator may select or input into the medical system that the patient has been moved, such as by selecting or pushing a reconnection button. In some embodiments, the medical system determines an intended patient move based on sensor output. For example, the medical system may be connected to a motion sensor, a proximity tag, RFID tag and/or any other system or method suitable for determining movement of the patient and/or medical system. In other embodiments, the medical system determines an intended patient move based on sensor output and operator input. For example, the medical system may detect that the patient has moved to the second location based on sensor output, but not determine that the patient has moved until the detected second location is confirmed by operator input.

In some embodiments, the sensors may be able to detect that a patient has moved to a second location because the spot of the second location has been input into the medical system. For example, the RFID tag may be able to determine hospital location based on other RFID tags or markers within the hospital. For example, a second proximity tag may be utilized in the second location, therefore, when the medical system is in range of the second proximity tag, the medical system knows that the patient has been moved to a second location.

If the medical system detects that the patient is in the second location, the medical system during the reconnection receiving operation 208 issues a check notification or receives a reconnection notice. The check notification notifies the operator that the patient is in the second location and requests operator input to confirm or deny that the patient is in the second location.

If the operator confirms the second location, the medical system during the reconnection receiving operation 208 receives a reconnection notice. In some embodiments, the operator confirms the second location by selecting or pushing a reconnection button. If the operator denies the second location, the medical system during the reconnection receiving operation 208 does not receive a reconnection notice. If the medical system during the reconnection receiving operation 208 does not receive a reconnection notice, then the medical system during the reconnection receiving operation 208 continues to monitor for the reconnection notice.

The ventilator or medical system during the connection determining operation 210 determines the connection status of each necessary hose based on the reconnection notice. As discussed above, the medical system determines a connection status of each necessary hose based on sensor output and/or operator input. Again, the medical system continues to check or update the connection statuses of the necessary hoses until the reconnection notification operation 212 ends.

The ventilator or medical system during the reconnection notification operation 212 issues a reconnection notification based on the determined connection statuses. The reconnection notification notifies the operator about whether the or not all of the necessary hoses have been reconnected to the patient based on the determined disconnection statuses by the connection determining operation 210. The reconnection notification is any suitable system or method for notifying an operator that the patient is either properly connected to medical system or not properly connected to the medial system, such as a visual, audio, and/or other sensory notification (e.g., vibration).

If the medical system during the reconnection notification operation 212 determines that any of the necessary hoses are not connected to the patient based on the received disconnection statuses, then the medical system determines that the patient is not properly connected to the medical system. If the patient is not properly connected, then the medical system issues a reconnection notification that informs the operator that the patient is not properly connected to the medical system or that at least one necessary hose still needs to be connected. If the patient is properly connected, then the medical system generates a reconnection notification that informs the operator that the patient is not properly connected to the medical system or that all of the necessary hoses are connected to the patient.

In some embodiments, the reconnection notification is displayed. FIG. 7 illustrates an embodiment of a screen shot of a reconnection notification 700. The displayed reconnection notification will indicate if the all of the necessary hoses have been reconnected to the patient or not. In some embodiments, the displayed reconnection notification may list each of the necessary hoses and the connection status of each of the necessary hoses. The disconnection status may be marked with icons, symbols, colors, animation, and/or any other suitable method for showing that a necessary hose is connected or disconnected. In some embodiments, the medical system during the reconnection notification operation 212 continuously updates the displayed reconnection notification based on the determined disconnection statuses until each of the necessary hoses has been connected and/or until operator input is received that ends the reconnection notification. In further embodiments, the reconnection notification may be displayed on a graphical user interface and be interactive with the operator. In this embodiment, the operator may be able to select a listed necessary hose and change the connection status of the selected necessary hose to connected and/or disconnected.

In other embodiments, the displayed reconnection notification lists only the necessary hoses that are disconnected as illustrated in FIG. 7. In this embodiment, the medical system during the reconnection notification operation 212 removes necessary hoses from the displayed reconnection notification as they become connected based on the determined connection statuses. Accordingly, in this embodiment, if the all of the necessary hoses are connected to the patient, then no necessary hoses are listed on the displayed reconnection notification.

As discussed above, operator input may end the reconnection notification operation 212. If the operator selects to end the reconnection notification operation 212, the medical system stops issuing the reconnection notification. Further, if the operator selects to end the reconnection notification, the medical system ends the connection determining operation 210. Alternatively, the reconnection notification operation 212 may end after the issuance of a reconnection notification or after a set amount of time after the issuance of reconnection notification that informs the operator that the all of the necessary hoses have been connected to the patent.

In one embodiment, method 200 is performed by the medical ventilator system illustrated in FIG. 1 and described above. In an alternative embodiment, a computer-readable medium having computer-executable instructions for performing methods for managing the move of a patient connected to a medical system are disclosed. These methods include repeatedly performing the steps illustrated in FIG. 2 and as described in the description of FIG. 2 above. In some embodiments, the medical system is a medical ventilator.

In another embodiment, the medical system includes: means for performing each of the operations illustrated in FIG. 2 and as described above in the description of FIG. 2. In one embodiment, the means for a medical ventilator system are illustrated in FIG. 1 and described in the above description of FIG. 1. However, the means described above for FIG. 1 and illustrated in FIG. 1 are but one example only and are not meant to be limiting.

Those skilled in the art will recognize that the methods and systems of the present disclosure may be implemented in many manners and as such are not to be limited by the foregoing exemplary embodiments and examples. In other words, functional elements being performed by a single or multiple components, in various combinations of hardware and software or firmware, and individual functions, can be distributed among software applications at either the client or server level or both. In this regard, any number of the features of the different embodiments described herein may be combined into single or multiple embodiments, and alternate embodiments having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software or firmware components described herein as would be understood by those skilled in the art now and hereafter.

Numerous other changes may be made which will readily suggest themselves to those skilled in the art and which are encompassed in the spirit of the disclosure and as defined in the claims. While various embodiments have been described for purposes of this disclosure, various changes and modifications may be made which are well within the scope of the present disclosure. Numerous other changes may be made which will readily suggest themselves to those skilled in the art and which are encompassed in the spirit of the disclosure and as defined in the claims.

What is claimed is:

1. A method comprising:
    displaying, on a user interface of a display screen, a listing of a plurality of hoses connected to a medical ventilator system, including a first hose and a second hose;
    identifying a first disconnection status of the first hose and a second disconnection status of the second hose;
    displaying, in the user interface concurrently with the listing of the plurality of hoses, a first marker indicating the first disconnection status and a second marker indicating the second disconnection status;
    based on the first disconnection status and the second disconnection status, generating a movement notification; and
    displaying, in the user interface, the movement notification.

2. The method of claim 1, wherein the first marker is at least one of an icon, symbol, color, or animation, and the second marker is at least one of an icon, symbol, color, or animation.

3. The method of claim 1, wherein the movement notification includes an indication of whether a patient is ready to be moved.

4. The method of claim 3, wherein the first disconnection status and the second disconnection status are one of: a connected status or a disconnected status.

5. The method of claim 4, wherein both the first disconnection status and the second disconnection status are the disconnected status, and the movement notification includes an indication that the patient is ready to be moved.

6. The method of claim 4, wherein either the first disconnection status or the second disconnection status is the connected status, and the movement notification includes an indication that the patient is not ready to be moved.

7. The method of claim 1, wherein a name of the first hose is displayed adjacent to the first marker and a name of the second hose is displayed adjacent to the second marker.

8. The method of claim 1, the method further comprising:
    identifying a change of the first disconnection status or the second disconnection status;
    based on the change, determining an updated notification; and
    displaying the updated notification.

9. The method of claim 1, wherein the movement notification is displayed concurrently with the first marker and the second marker.

10. The method of claim 1, wherein the first hose is one of a ventilation tubing circuit, a flow sensor hose, or an oximeter cable.

11. A ventilator, comprising:
    a display screen;
    a plurality of hoses connected to the ventilator, including a first hose and a second hose;
    a processor; and
    a memory storing computer executable instructions that when executed by the processor cause the ventilator to perform a set of operations comprising:
        displaying, on a user interface of the display screen, a listing of the plurality of hoses connected to the ventilator;
        identifying a first disconnection status of the first hose and a second disconnection status of the second hose;
        displaying, in the user interface concurrently with the listing of the plurality of hoses, a first marker indicating the first disconnection status and a second marker indicating the second disconnection status;
        based on the first disconnection status and the second disconnection status, generating a movement notification; and
        displaying, in the user interface, the movement notification.

12. The ventilator of claim 11, wherein the first marker is at least one of an icon, symbol, color, or animation, and the second marker is at least one of an icon, symbol, color, or animation.

13. The ventilator of claim 11, wherein the movement notification includes an indication of whether a patient is ready to be moved.

14. The ventilator of claim 13, wherein the first disconnection status and the second disconnection status are one of: a connected status or a disconnected status.

15. The ventilator of claim 14, wherein both the first disconnection status and the second disconnection status are the disconnected status, and the movement notification includes an indication that the patient is ready to be moved.

16. The ventilator of claim 14, wherein either the first disconnection status or the second disconnection status is the connected status, and the movement notification includes an indication that the patient is not ready to be moved.

17. The ventilator of claim 11, the set of operations further comprising:
    identifying a change of the first disconnection status or the second disconnection status;
    based on the change, issuing an updated notification; and
    displaying the updated notification.

18. The ventilator of claim 11, wherein the first hose is one of a ventilation tubing circuit, a flow sensor hose, or an oximeter cable.

19. A ventilator, comprising:
    a display screen;
    a plurality of hoses connected to the ventilator, including a first hose and a second hose;
    a processor; and
    a memory storing computer executable instructions that when executed by the processor cause the ventilator to perform a set of operations comprising:
        receiving an indication of an intended patient disconnection;

based on receiving the indication, displaying, on a user interface of the display screen, a listing of the plurality of hoses connected to the ventilator;

identifying a disconnected status for a first hose in the plurality of hoses;

identifying a connected status for a second hose in the plurality of hoses;

displaying, in the user interface concurrently with the listing of the plurality of hoses, a first marker indicating the disconnected status of the first hose and a second marker indicating the connected status of the second hose;

based on the connected status of the second hose, generating a movement notification that the patient is not ready to be moved; and displaying, in the user interface, the movement notification.

20. The ventilator of claim 19, wherein the first hose is one of a ventilation tubing circuit, a flow sensor hose, or an oximeter cable and wherein the first marker is at least one of an icon, symbol, color, or animation.

* * * * *